United States Patent
Wybo et al.

(10) Patent No.: US 11,399,777 B2
(45) Date of Patent: Aug. 2, 2022

(54) INTRAOPERATIVE NEURAL MONITORING SYSTEM AND METHOD

(71) Applicant: Depuy Synthes Products, Inc., Raynham, MA (US)

(72) Inventors: Christopher Wybo, Brighton, MI (US); Darren Scarfe, LaSalle (CA); Aashish Shah, Ann Arbor, MI (US); Jacob A. Marks, Mansfield, MA (US); James G. Lee, South Weymouth, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 488 days.

(21) Appl. No.: 16/586,121

(22) Filed: Sep. 27, 2019

(65) Prior Publication Data
US 2021/0093228 A1    Apr. 1, 2021

(51) Int. Cl.
*A61B 5/00* (2006.01)
*A61B 5/11* (2006.01)
*G06T 11/20* (2006.01)

(52) U.S. Cl.
CPC ............ *A61B 5/743* (2013.01); *A61B 5/1104* (2013.01); *A61B 5/1107* (2013.01);
(Continued)

(58) Field of Classification Search
CPC ..... A61B 5/389; A61B 5/1104; A61B 5/1106; A61B 5/1107; A61B 34/25; A61B 5/224;
(Continued)

(56) References Cited

U.S. PATENT DOCUMENTS 3,200,814 A    8/1965  Taylor et al.
3,565,080 A    2/1971  Ide
(Continued)

FOREIGN PATENT DOCUMENTS

EP    1417000 A2    5/2004
EP    1575010 A1    9/2005
(Continued)

OTHER PUBLICATIONS

J. Herdmann MD; V. Deletis MD PhD; H.Edmonds PhD; N. Morota MD, Spinal Cord and Nerve Root Monitoring in Spine Surgery and Related Procedures, Spine Journal, Apr. 1, 1996, pp. 879-885, vol. 21.

(Continued)

*Primary Examiner* — David J. McCrosky
(74) *Attorney, Agent, or Firm* — Condo Roccia Koptiw LLP

(57) ABSTRACT

A neuromuscular sensing method includes transmitting an electrical stimulus from a distal end portion of an elongate stimulator extending within an intracorporeal treatment area of a subject and detecting an artificially induced response of at least two muscles of the subject in response to the transmitted electrical stimulus, each response being detected by a respective sensor in mechanical communication with the muscle. A graphical user interface (GUI) is transitioned from a first state to a second state; the first state indicating to the transmission of a stimulus with no artificially induced response detected, and the second state indicating the detection of the artificially induced response of the at least two muscles, and further identifying one of the at least two muscles as a primary muscle response.

20 Claims, 5 Drawing Sheets

(52) U.S. Cl.
CPC .......... *A61B 5/4893* (2013.01); *G06T 11/206* (2013.01); *A61B 2562/0219* (2013.01)

(58) Field of Classification Search
CPC .......... A61B 5/375; A61B 5/395; A61B 5/397; A61B 5/384; A61B 5/4519; A61B 5/4029; A61B 5/4035; A61B 5/4041; A61B 5/4047; A61B 5/4052; A61B 5/40; A61B 5/4058; A61B 5/742; A61B 5/7425; A61B 5/743; A61B 5/7435; A61B 5/744; A61B 5/7445; A61N 1/37247; A63B 2213/004
USPC .................................................. 600/546, 554
See application file for complete search history.

(56) References Cited

U.S. PATENT DOCUMENTS

| | | | |
|---|---|---|---|
| 3,797,010 A | 3/1974 | Adler et al. |
| 4,155,353 A | 5/1979 | Rea et al. |
| 4,493,327 A | 1/1985 | Bergelson et al. |
| 4,807,642 A | 2/1989 | Brown |
| 4,817,628 A | 4/1989 | Zealear et al. |
| 4,940,453 A | 7/1990 | Cadwell |
| 4,994,015 A | 2/1991 | Cadwell |
| 5,047,005 A | 9/1991 | Cadwell |
| 5,078,674 A | 1/1992 | Cadwell |
| 5,116,304 A | 5/1992 | Cadwell |
| 5,178,145 A | 1/1993 | Rea |
| 5,284,153 A | 2/1994 | Raymond et al. |
| 5,284,154 A | 2/1994 | Raymond et al. |
| 5,482,038 A | 1/1996 | Ruff |
| 5,566,678 A | 10/1996 | Cadwell |
| 5,593,429 A | 1/1997 | Ruff |
| 5,631,667 A | 5/1997 | Cadwell |
| 5,775,331 A | 7/1998 | Raymond et al. |
| 5,860,939 A | 1/1999 | Wofford et al. |
| 5,888,370 A | 3/1999 | Becker et al. |
| 5,993,630 A | 11/1999 | Becker et al. |
| 5,993,632 A | 11/1999 | Becker et al. |
| 6,030,401 A | 2/2000 | Marino |
| 6,093,205 A | 7/2000 | McLeod et al. |
| 6,181,961 B1 | 1/2001 | Prass |
| 6,183,518 B1 | 2/2001 | Ross et al. |
| 6,206,921 B1 | 3/2001 | Guagliano et al. |
| 6,221,082 B1 | 4/2001 | Marino et al. |
| 6,224,603 B1 | 5/2001 | Marino |
| 6,251,140 B1 | 6/2001 | Marino et al. |
| 6,264,659 B1 | 7/2001 | Ross et al. |
| 6,266,394 B1 | 7/2001 | Marino |
| 6,266,558 B1 | 7/2001 | Gozani et al. |
| 6,280,447 B1 | 8/2001 | Marino et al. |
| 6,287,832 B1 | 9/2001 | Becker et al. |
| 6,290,724 B1 | 9/2001 | Marino |
| 6,312,443 B1 | 11/2001 | Stone |
| 6,324,432 B1 | 11/2001 | Rigaux et al. |
| 6,361,508 B1 | 3/2002 | Johnson et al. |
| 6,368,325 B1 | 4/2002 | McKinley et al. |
| 6,387,070 B1 | 5/2002 | Marino et al. |
| 6,387,130 B1 | 5/2002 | Stone et al. |
| 6,436,143 B1 | 8/2002 | Ross et al. |
| 6,466,817 B1 | 10/2002 | Kaula et al. |
| 6,478,805 B1 | 11/2002 | Marino et al. |
| 6,485,518 B1 | 11/2002 | Cornwall et al. |
| 6,491,626 B1 | 12/2002 | Stone et al. |
| 6,500,128 B2 | 12/2002 | Marino |
| 6,519,319 B1 | 2/2003 | Marino et al. |
| 6,530,930 B1 | 3/2003 | Marino et al. |
| 6,533,797 B1 | 3/2003 | Stone et al. |
| 6,540,747 B1 | 4/2003 | Marino |
| 6,564,078 B1 | 5/2003 | Marino et al. |
| 6,638,281 B2 | 10/2003 | Gorek |
| 6,641,708 B1 | 11/2003 | Becker et al. |
| 6,654,634 B1 | 11/2003 | Prass |
| 6,739,112 B1 | 5/2004 | Marino |
| 6,760,616 B2 | 7/2004 | Hoey et al. |
| 6,764,452 B1 | 7/2004 | Gillespie et al. |
| 6,764,489 B2 | 7/2004 | Ferree |
| 6,802,844 B2 | 10/2004 | Ferree |
| 6,805,668 B1 | 10/2004 | Cadwell |
| 6,807,438 B1 | 10/2004 | Brun Del Re et al. |
| 6,843,790 B2 | 1/2005 | Ferree |
| 6,852,126 B2 | 2/2005 | Ahlgren |
| 6,870,109 B1 | 3/2005 | Villarreal |
| 6,887,248 B2 | 5/2005 | McKinley et al. |
| 6,923,814 B2 | 8/2005 | Hildebrand et al. |
| 6,945,973 B2 | 9/2005 | Bray |
| 6,964,674 B1 | 11/2005 | Matsuura et al. |
| 6,972,199 B2 | 12/2005 | Lebouitz et al. |
| 6,981,990 B2 | 1/2006 | Keller |
| 7,001,432 B2 | 2/2006 | Keller et al. |
| 7,025,769 B1 | 4/2006 | Ferree |
| 7,050,848 B2 | 5/2006 | Hoey et al. |
| 7,072,521 B1 | 7/2006 | Cadwell |
| 7,079,883 B2 | 7/2006 | Marino et al. |
| 7,160,303 B2 | 1/2007 | Keller |
| 7,162,850 B2 | 1/2007 | Marino et al. |
| 7,166,113 B2 | 1/2007 | Arambula et al. |
| 7,175,662 B2 | 2/2007 | Link et al. |
| 7,177,677 B2 | 2/2007 | Kaula et al. |
| 7,207,949 B2 | 4/2007 | Miles et al. |
| 7,214,197 B2 | 5/2007 | Prass |
| 7,214,225 B2 | 5/2007 | Ellis et al. |
| 7,216,001 B2 | 5/2007 | Hacker et al. |
| 7,230,688 B1 | 6/2007 | Villarreal |
| 7,236,832 B2 | 6/2007 | Hemmerling et al. |
| 7,267,691 B2 | 9/2007 | Keller et al. |
| 7,296,500 B1 | 11/2007 | Martinelli |
| 7,320,689 B2 | 1/2008 | Keller |
| 7,338,531 B2 | 3/2008 | Ellis et al. |
| 7,341,590 B2 | 3/2008 | Ferree |
| 7,367,958 B2 | 5/2008 | McBean et al. |
| 7,374,448 B1 | 5/2008 | Jepsen et al. |
| 7,379,767 B2 | 5/2008 | Rea |
| 7,470,236 B1 | 12/2008 | Kelleher et al. |
| 7,485,146 B1 | 2/2009 | Crook et al. |
| 7,522,953 B2 | 4/2009 | Kaula et al. |
| 7,527,629 B2 | 5/2009 | Link et al. |
| 7,527,649 B1 | 5/2009 | Blain |
| 7,553,307 B2 | 6/2009 | Bleich et al. |
| 7,555,343 B2 | 6/2009 | Bleich |
| 7,569,067 B2 | 8/2009 | Keller |
| 7,578,819 B2 | 8/2009 | Bleich et al. |
| 7,582,058 B1 | 9/2009 | Miles et al. |
| 7,583,991 B2 | 9/2009 | Rea |
| 7,611,522 B2 | 11/2009 | Gorek |
| 7,618,423 B1 | 11/2009 | Valentine et al. |
| 7,628,813 B2 | 12/2009 | Link |
| 7,634,315 B2 | 12/2009 | Cholette |
| 7,657,308 B2 | 2/2010 | Miles et al. |
| 7,664,544 B2 | 2/2010 | Miles et al. |
| 7,666,195 B2 | 2/2010 | Kelleher et al. |
| 7,668,588 B2 | 2/2010 | Kovacs |
| 7,691,057 B2 | 4/2010 | Miles et al. |
| 7,693,562 B2 | 4/2010 | Marino et al. |
| 7,708,776 B1 | 5/2010 | Blain et al. |
| 7,713,463 B1 | 5/2010 | Reah et al. |
| 7,722,613 B2 | 5/2010 | Sutterlin et al. |
| 7,722,673 B2 | 5/2010 | Keller |
| 7,738,968 B2 | 6/2010 | Bleich |
| 7,738,969 B2 | 6/2010 | Bleich |
| 7,740,631 B2 | 6/2010 | Bleich et al. |
| 7,766,816 B2 | 8/2010 | Chin et al. |
| 7,776,049 B1 | 8/2010 | Curran et al. |
| 7,776,094 B2 | 8/2010 | McKinley et al. |
| 7,785,248 B2 | 8/2010 | Annest et al. |
| 7,785,253 B1 | 8/2010 | Arambula et al. |
| 7,815,682 B1 | 10/2010 | Peterson et al. |
| 7,819,801 B2 | 10/2010 | Miles et al. |
| 7,828,855 B2 | 11/2010 | Ellis et al. |
| 7,833,251 B1 | 11/2010 | Ahlgren et al. |
| 7,857,813 B2 | 12/2010 | Schmitz et al. |
| 7,862,592 B2 | 1/2011 | Peterson et al. |
| 7,862,614 B2 | 1/2011 | Keller et al. |

(56) References Cited

U.S. PATENT DOCUMENTS

| | | |
|---|---|---|
| 7,867,277 B1 | 1/2011 | Tohmeh |
| 7,883,527 B2 | 2/2011 | Matsuura et al. |
| 7,887,538 B2 | 2/2011 | Bleich et al. |
| 7,887,568 B2 | 2/2011 | Ahlgren |
| 7,887,595 B1 | 2/2011 | Pimenta |
| 7,892,173 B2 | 2/2011 | Miles et al. |
| 7,901,430 B2 | 3/2011 | Matsuura et al. |
| 7,905,840 B2 | 3/2011 | Pimenta et al. |
| 7,905,886 B1 | 3/2011 | Curran et al. |
| 7,914,350 B1 | 3/2011 | Bozich et al. |
| 7,918,849 B2 | 4/2011 | Bleich et al. |
| 7,918,891 B1 | 4/2011 | Curran et al. |
| 7,920,922 B2 | 4/2011 | Gharib et al. |
| 7,927,337 B2 | 4/2011 | Keller |
| 7,935,051 B2 | 5/2011 | Miles et al. |
| 7,938,830 B2 | 5/2011 | Saadat et al. |
| 7,942,104 B2 | 5/2011 | Butcher et al. |
| 7,942,826 B1 | 5/2011 | Scholl et al. |
| 7,946,236 B2 | 5/2011 | Butcher |
| 7,959,577 B2 | 6/2011 | Schmitz et al. |
| 7,962,191 B2 | 6/2011 | Marino et al. |
| 7,963,915 B2 | 6/2011 | Bleich |
| 7,963,927 B2 | 6/2011 | Kelleher et al. |
| 7,981,058 B2 | 7/2011 | Akay |
| 7,981,144 B2 | 7/2011 | Geist et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,012,212 B2 | 9/2011 | Link et al. |
| 8,016,767 B2 | 9/2011 | Miles et al. |
| 8,016,776 B2 | 9/2011 | Bourget et al. |
| 8,027,716 B2 | 9/2011 | Gharib et al. |
| 8,048,080 B2 | 11/2011 | Bleich et al. |
| 8,050,769 B2 | 11/2011 | Gharib et al. |
| 8,055,349 B2 | 11/2011 | Gharib et al. |
| 8,062,298 B2 | 11/2011 | Schmitz et al. |
| 8,062,300 B2 | 11/2011 | Schmitz et al. |
| 8,062,369 B2 | 11/2011 | Link |
| 8,062,370 B2 | 11/2011 | Keller et al. |
| 8,063,770 B2 | 11/2011 | Costantino |
| 8,068,912 B2 | 11/2011 | Kaula et al. |
| 8,070,812 B2 | 12/2011 | Keller |
| 8,074,591 B2 | 12/2011 | Butcher et al. |
| 8,075,499 B2 | 12/2011 | Nathan et al. |
| 8,075,601 B2 | 12/2011 | Young |
| 8,083,685 B2 | 12/2011 | Fagin et al. |
| 8,083,796 B1 | 12/2011 | Raiszadeh et al. |
| 8,088,163 B1 | 1/2012 | Kleiner |
| 8,088,164 B2 | 1/2012 | Keller |
| 8,090,436 B2 | 1/2012 | Hoey et al. |
| 8,092,455 B2 | 1/2012 | Neubardt et al. |
| 8,092,456 B2 | 1/2012 | Bleich et al. |
| 8,103,339 B2 | 1/2012 | Rea |
| 8,114,019 B2 | 2/2012 | Miles et al. |
| 8,114,162 B1 | 2/2012 | Bradley |
| 8,123,668 B2 | 2/2012 | Annest et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,147,551 B2 | 4/2012 | Link et al. |
| 8,165,653 B2 | 4/2012 | Marino et al. |
| 8,167,915 B2 | 5/2012 | Ferree et al. |
| 8,172,750 B2 | 5/2012 | Miles et al. |
| 8,206,312 B2 | 6/2012 | Farquhar |
| 8,255,044 B2 | 8/2012 | Miles et al. |
| 8,255,045 B2 | 8/2012 | Gharib et al. |
| 8,303,515 B2 | 11/2012 | Miles et al. |
| 8,337,410 B2 | 12/2012 | Kelleher et al. |
| 8,343,065 B2 | 1/2013 | Bartol et al. |
| 8,343,079 B2 | 1/2013 | Bartol et al. |
| 8,394,129 B2 | 3/2013 | Morgenstern Lopez et al. |
| 8,500,653 B2 | 8/2013 | Farquhar |
| 8,500,738 B2 | 8/2013 | Wolf, II |
| 8,517,954 B2 | 8/2013 | Bartol et al. |
| 8,535,224 B2 | 9/2013 | Cusimano Reaston et al. |
| 8,538,539 B2 | 9/2013 | Gharib et al. |
| 8,556,808 B2 | 10/2013 | Miles et al. |
| 8,562,539 B2 | 10/2013 | Marino |
| 8,562,660 B2 | 10/2013 | Peyman |
| 8,568,317 B1 | 10/2013 | Gharib et al. |
| 8,591,431 B2 | 11/2013 | Calancie et al. |
| 8,641,638 B2 | 2/2014 | Kelleher et al. |
| 8,731,654 B2 | 5/2014 | Johnson et al. |
| 8,784,330 B1 | 7/2014 | Scholl et al. |
| 8,792,977 B2 | 7/2014 | Kakei et al. |
| 8,855,822 B2 | 10/2014 | Bartol et al. |
| 8,864,654 B2 | 10/2014 | Kleiner et al. |
| 8,936,626 B1 | 1/2015 | Tohmeh et al. |
| 8,945,004 B2 | 2/2015 | Miles et al. |
| 8,958,869 B2 | 2/2015 | Kelleher et al. |
| 8,982,593 B2 | 3/2015 | Nondahl et al. |
| 8,989,855 B2 | 3/2015 | Murphy et al. |
| 8,989,866 B2 | 3/2015 | Gharib et al. |
| 9,014,776 B2 | 4/2015 | Marino et al. |
| 9,014,797 B2 | 4/2015 | Shiffman et al. |
| 9,037,250 B2 | 5/2015 | Kaula et al. |
| 9,039,630 B2 * | 5/2015 | Bartol .................. A61B 5/1104 600/554 |
| 9,066,701 B1 | 6/2015 | Finley et al. |
| 9,084,551 B2 | 7/2015 | Brunnett et al. |
| 9,131,947 B2 | 9/2015 | Ferree |
| 9,192,415 B1 | 11/2015 | Arnold et al. |
| 9,295,396 B2 | 3/2016 | Gharib et al. |
| 9,295,401 B2 | 3/2016 | Cadwell |
| 9,301,711 B2 | 4/2016 | Bartol et al. |
| 9,392,953 B1 | 7/2016 | Gharib |
| 9,446,259 B2 | 9/2016 | Phillips et al. |
| 2001/0031916 A1 | 10/2001 | Bennett et al. |
| 2002/0038092 A1 | 3/2002 | Stanaland et al. |
| 2002/0165590 A1 | 11/2002 | Crowe et al. |
| 2003/0074037 A1 | 4/2003 | Moore et al. |
| 2004/0077969 A1 | 4/2004 | Onda et al. |
| 2004/0082877 A1 | 4/2004 | Kouou et al. |
| 2004/0186535 A1 | 9/2004 | Knowlton |
| 2004/0230138 A1 | 11/2004 | Inoue et al. |
| 2004/0243018 A1 | 12/2004 | Organ et al. |
| 2005/0075578 A1 | 4/2005 | Gharib et al. |
| 2005/0085741 A1 | 4/2005 | Hoskonen et al. |
| 2005/0102007 A1 | 5/2005 | Ayal et al. |
| 2005/0240086 A1 | 10/2005 | Akay |
| 2005/0245839 A1 | 11/2005 | Stivoric et al. |
| 2005/0280531 A1 | 12/2005 | Fadem et al. |
| 2005/0283204 A1 | 12/2005 | Buhlmann et al. |
| 2006/0020177 A1 | 1/2006 | Seo et al. |
| 2006/0052726 A1 | 3/2006 | Weisz et al. |
| 2006/0135888 A1 | 6/2006 | Mimnagh-Kelleher et al. |
| 2006/0270949 A1 | 11/2006 | Mathie et al. |
| 2007/0038155 A1 | 2/2007 | Kelly et al. |
| 2007/0049826 A1 | 3/2007 | Willis |
| 2007/0232958 A1 | 10/2007 | Donofrio et al. |
| 2007/0265675 A1 | 11/2007 | Lund et al. |
| 2007/0276270 A1 | 11/2007 | Tran |
| 2008/0051643 A1 | 2/2008 | Park et al. |
| 2008/0058656 A1 | 3/2008 | Costello et al. |
| 2008/0167695 A1 | 7/2008 | Tehrani et al. |
| 2008/0234767 A1 | 9/2008 | Salmon et al. |
| 2008/0306363 A1 | 12/2008 | Chaiken et al. |
| 2008/0306397 A1 | 12/2008 | Bonmassar et al. |
| 2008/0312560 A1 | 12/2008 | Jamsen et al. |
| 2008/0312709 A1 | 12/2008 | Volpe et al. |
| 2009/0036747 A1 | 2/2009 | Hayter et al. |
| 2009/0062696 A1 | 3/2009 | Nathan et al. |
| 2009/0069709 A1 | 3/2009 | Schmitz et al. |
| 2009/0069722 A1 | 3/2009 | Flaction et al. |
| 2009/0076336 A1 | 3/2009 | Mazar et al. |
| 2009/0171381 A1 | 7/2009 | Schmitz et al. |
| 2009/0192413 A1 | 7/2009 | Sela et al. |
| 2009/0228068 A1 | 9/2009 | Buhlmann et al. |
| 2009/0247910 A1 | 10/2009 | Klapper |
| 2009/0306741 A1 | 12/2009 | Hogle et al. |
| 2009/0318779 A1 | 12/2009 | Bao |
| 2010/0137748 A1 | 6/2010 | Sone et al. |
| 2010/0152619 A1 | 6/2010 | Kalpaxis et al. |
| 2010/0152622 A1 | 6/2010 | Teulings |

(56) References Cited

U.S. PATENT DOCUMENTS

| | | | |
|---|---|---|---|
| 2010/0152623 A1 | 6/2010 | Williams | |
| 2010/0168559 A1 | 7/2010 | Tegg et al. | |
| 2010/0262042 A1 | 10/2010 | Kim | |
| 2010/0292617 A1 | 11/2010 | Lei et al. | |
| 2011/0004207 A1 | 1/2011 | Wallace et al. | |
| 2011/0230782 A1 | 9/2011 | Bartol et al. | |
| 2011/0237974 A1 | 9/2011 | Bartol et al. | |
| 2011/0270121 A1 | 11/2011 | Johnson et al. | |
| 2011/0301665 A1 | 12/2011 | Mercanzini et al. | |
| 2012/0053491 A1 | 3/2012 | Nathan et al. | |
| 2012/0191003 A1 | 7/2012 | Garabedian et al. | |
| 2013/0197321 A1 | 8/2013 | Wilson | |
| 2013/0204097 A1 | 8/2013 | Rondoni et al. | |
| 2013/0213659 A1 | 8/2013 | Luyster et al. | |
| 2013/0253533 A1 | 9/2013 | Bartol et al. | |
| 2014/0020178 A1 | 1/2014 | Stashuk et al. | |
| 2014/0066803 A1 | 3/2014 | Choi | |
| 2014/0088029 A1 | 3/2014 | Sugimoto et al. | |
| 2014/0121555 A1* | 5/2014 | Scott ........................ | A61B 5/24 600/546 |
| 2014/0148725 A1 | 5/2014 | Cadwell | |
| 2014/0163411 A1 | 6/2014 | Rea | |
| 2014/0275926 A1 | 9/2014 | Scott et al. | |
| 2014/0276195 A1 | 9/2014 | Papay et al. | |
| 2014/0358026 A1 | 12/2014 | Mashiach et al. | |
| 2015/0032022 A1 | 1/2015 | Stone et al. | |
| 2015/0045783 A1 | 2/2015 | Edidin | |
| 2015/0051506 A1 | 2/2015 | Wybo et al. | |
| 2015/0112325 A1 | 4/2015 | Whitman | |
| 2015/0230749 A1 | 8/2015 | Gharib et al. | |
| 2015/0342521 A1 | 12/2015 | Narita et al. | |
| 2015/0342621 A1 | 12/2015 | Jackson, III | |
| 2016/0051812 A1 | 2/2016 | Montgomery, Jr. et al. | |

FOREIGN PATENT DOCUMENTS

| | | |
|---|---|---|
| EP | 2231003 A1 | 9/2010 |
| EP | 2535082 A1 | 12/2012 |
| FR | 2920087 A1 | 2/2009 |
| WO | 0078209 A2 | 12/2000 |
| WO | 2007024147 A1 | 3/2007 |
| WO | 2014160832 A2 | 10/2014 |
| WO | 2015171619 A1 | 11/2015 |
| WO | 2016100340 A1 | 6/2016 |

OTHER PUBLICATIONS

N. Hollands MB, BS; J. Kostuik. Continuous Electromyographic Moniotring to Detect Nerve Root Injury During Thoracolumbar Scoliosis Surgery, Spine Journal, Nov. 1, 1997, pp. 2547-2550, vol. 22, Issue 21.

C. Harper, J. Daube, Facial Nerve Electromyography and Other Cranial Nerve Monitoring, Journal of Clinical Neurophysiology, May 1998, pp. 206-216, vol. 15, Issue 3.

D. Beck, J. Ben Ecke Jr, Intraoperative Facial Nerve Monitoring Technical Aspects, Official Journal of the American Academy of Otolaryngology-Head and Neck Surgery Foundation, Apr. 27, 1989.

W. Welch MD, R. Rose PhD, J. Balzer PhD, G. Jacobs, MD, Evaluation with evoked and spontaneous electromyography during lumbar instrumentation: a prospective study, Journal of Neurosurgery, Sep. 1997, pp. 397-402, vol. 87, No. 3.

W. Young MD, D. Morledge PhD, W. Martin PhD, K. Park MD, Intraoperative Stimulation of Pedicle Screws: A New Method for Verification of Screw Placement, Journal of Neurosurgery, 1995, pp. 544-547 vol. 44.

K. Sugita MD, S. Kobayashi MD, Technical and instrumental improvements in the surgical treatment of acoustic neurinomas, Journal of Neurosurgery, Dec. 1982, pp. 747-752, vol. 57.

J. Boston, L. Deneault, Sensory evoked potentials: a system for clinical testing and patient monitoring, International Journal of Clinical Monitoring and Computing, 1984, pp. 13-19, Martinus Nijhoff Publishers, Netherlands.

A. Moller, Neuromonitoring in Operations in the Skull Base, The Keio Journal of Medicine, Oct. 1991, pp. 151-159.

J. Maurer, H. Pelster, W. Mann, Intraoperatives Monitoring motorischer Hurnnerven bei Operationen an Hals und Schadelbasis, Laryngo-Rhino-Otol, pp. 561-567, vol. 73.

N. Friedman MD, M. Curran R. EPT, Somatosensory Evoked Potentials after Sequential Extremity Stimulation: A New Method for Improved Monitoring Accuracy, Neurosurgery, 1987, pp. 755-758, vol. 21, No. 5.

R. Gopalan, P. Parker, R. Scott, Microprocessor-Based System for Monitoring Spinal Evoked Potentials During Surgery, IEEE Transactions on Biomedical Engineering, Oct. 1986, pp. 982-985, vol. BME-22, No. 10.

B. Moed MD, B. Ahmad MD, J. Craig MD, G. Jacobson PhD, M. Anders MD, Intraoperative Monitoring with Stimulus-Evoked Electromyography during Placement Iliosacral Screws, The Journal of Bone and Joint Surgery, Apr. 1998, pp. 537-546, vol. 80-A, No. 4, The Journal of Bone and Joint Surgery, Inc.

C. Yingling PhD, J. Gardi PhD, Intraoperative Monitoring of Facial and Cochlear Nerves During Acoustic Neuroma Surgery, Acoustic Neuroma I, Apr. 1992, pp. 413-448, vol. 25, No. 2, Otolaryngologic Clinics of North America.

N. Holland MB, BS, J. Kostuik MD, Continuous Electromyographic Monitoring to Detect Nerve Root Injury During Thoracolumbar Scoliosis Surgery, Spine, 1997, pp. 2547-2550, vol. 22, No. 21, Lippincott-Raven Publishers.

P. Dulguerov, F. Marchal, W. Lehmann, Postparotidectomy Facial Nerve Paralysis: Possible Etiologic Factors and Results with Routine Facial Nerve Monitoring, The Laryngoscope, May 1999, pp. 754-762 vol. 109, Lippincott Williams & Wilkins, Inc. Philadelphia, Pennsylvania.

M. Imai MS, Y. Harada MD, Y. Atsuta MD, Y. Takemitsu MD, T. Iwahara MD, Automated Spinal Cord Monitoring for Spinal Surgery, Paraplegia, 1989, pp. 204-211.

R. Witt, Facial nerve monitoring in parotid surgery: The standard of care?, Otolaryngology-Head and Neck Surgery, Nov. 1998, pp. 468-470, vol. 119, No. 5.

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference BIOSIGNAL 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

(56) References Cited

OTHER PUBLICATIONS

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

* cited by examiner

US 11,399,777 B2

INTRAOPERATIVE NEURAL MONITORING SYSTEM AND METHOD

TECHNICAL FIELD

The present disclosure relates generally to a sensing device used with a surgical diagnostic system for detecting artificially induced neuromuscular activity.

BACKGROUND

Traditional surgical practices emphasize the importance of recognizing or verifying the location of nerves to avoid injuring them. Advances in surgical techniques include development of techniques including ever smaller exposures, such as minimally invasive surgical procedures, and the insertion of ever more complex medical devices. With these advances in surgical techniques, there is a corresponding need for improvements in methods of detecting and/or avoiding nerves.

SUMMARY

Provided herein is an intraoperative neural monitoring system, and a neuromuscular sensing method that is operative to promptly alert a user to the occurrence of an artificially induced muscle response during a surgical procedure. Such a response is indicative of the presence of a nerve within an intracorporeal treatment area and would suggest caution to the user/surgeon. Conversely, a lack of a response is also informative and would suggest no nerve in the immediate area.

An embodiment of the method includes transmitting an electrical stimulus from a distal end portion of an elongate stimulator extending within an intracorporeal treatment area of a subject, and detecting an artificially induced response of at least two muscles of the subject in response to the transmitted electrical stimulus, each response being detected by a respective sensor in mechanical communication with the muscle. Following the detection, a graphical user interface (GUI) is transitioned from a first state to a second state. The first state indicates the transmission of a stimulus with no artificially induced response detected, and the second state indicates the detection of the artificially induced response of the at least two muscles. The second state further identifies one of the at least two muscles as providing the primary muscle response.

An embodiment of the intraoperative neural monitoring system includes a plurality of mechanical sensors, an elongate stimulator, and a host system. Each of the plurality of mechanical sensors is operative to monitor a different muscle of a subject. The elongate stimulator is operative to extend within an intracorporeal treatment area of a subject and to transmit an electrical stimulus from a distal end portion, and the host system is in communication with the plurality of mechanical sensors.

The host system includes a display and a processor. The processor is configured to receive an output signal from each of the mechanical sensors, where the output signal corresponding to the movement of the monitored muscles of the subject. It is further configured to display a graphical user interface (GUI) via the display, and detect an artificially induced response of at least two muscles of the subject in response to the electrical stimulus. The processor is configured to transition the GUI from a first state to a second state in response to the detected artificially induced response of the at least two muscles. The first state indicates the transmission of a stimulus with no artificially induced response detected, and the second state indicates the detection of the artificially induced response of the at least two muscles, while further identifying one of the at least two muscles as a primary muscle response.

The features and advantages and other features and advantages of the present technology are readily apparent from the following detailed description when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

The present disclosure provides a system that enables a surgeon/user to rapidly identify the presence of nerves within a surgical area internal to a subject. Such a system may be useful, for example, during spinal surgery, where there is a myriad of nerve bundles exiting the spine and extending through adjacent muscle tissue. The present technology relies on understanding that when a nerve is depolarized, the muscles innervated by that nerve contract. The present system is operative to monitor certain muscle groups of the subject and discriminate between muscle motion that is artificially induced by a transmitted electrical stimulus, muscle motion that is artificially induced, though not by a transmitted electrical stimulus (i.e., a "spontaneous response" which may be caused, for example, by mechanical strain), or other intended or environmental motion. If the system detects an artificially induced response to a transmitted stimulus, or a spontaneous response, it may transition a graphical user interface from a generic "stimulating" state to a more specific detection state. The detection state may identify the type of response, as well as all muscles that exhibit motion characteristic of that type of response. Furthermore, the system may alert the surgeon to which muscle is presenting the primary response to the depolarized nerve, and which are presenting ancillary responses (with the understanding that one nerve root may innervate multiple muscle groups to differing degrees).

Figure 1:
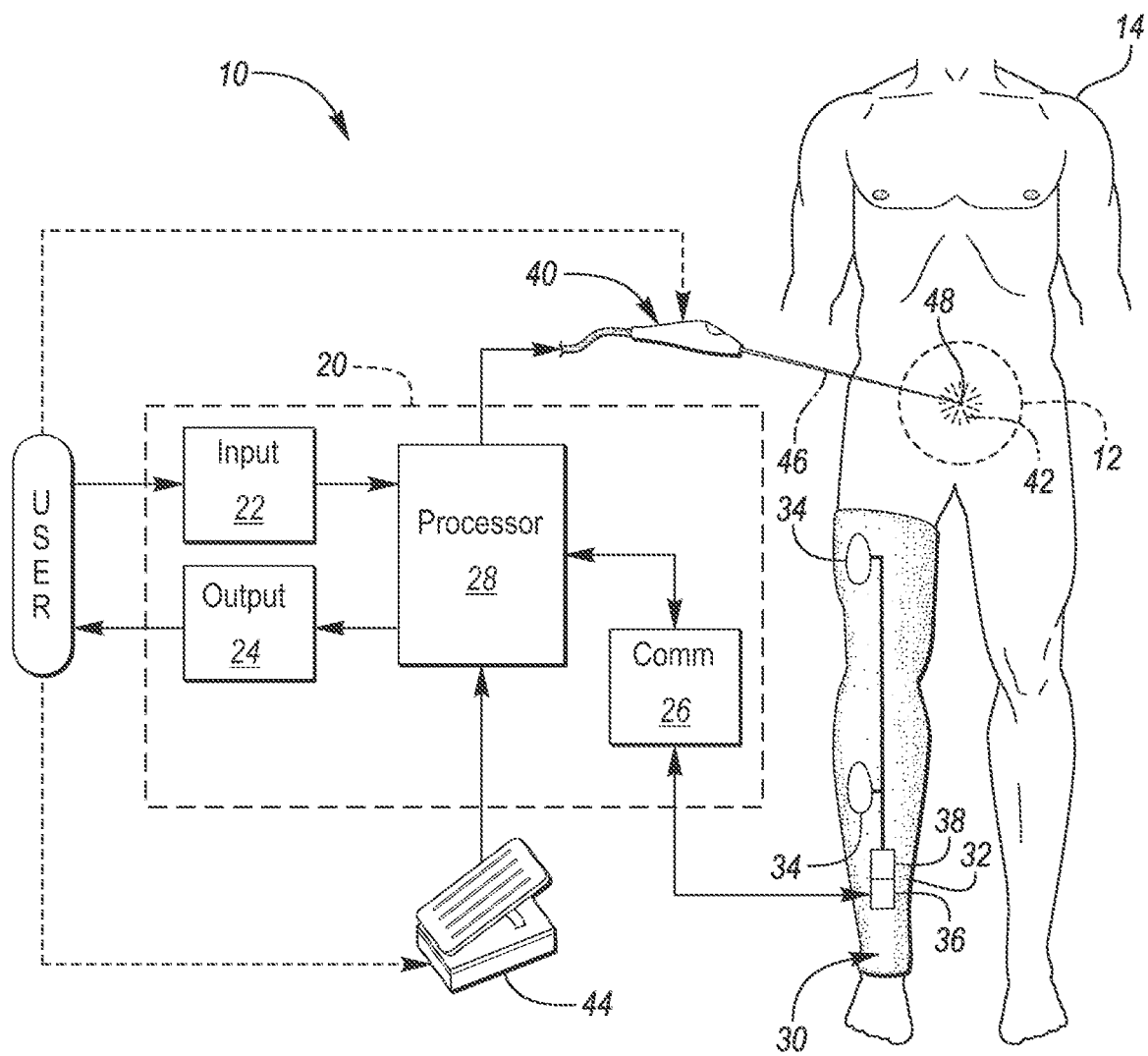
FIG. 1 is a schematic diagram of a neural monitoring system, including a sleeve-based sensing device, for detecting an artificially-induced mechanical muscle response.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14, such as during a surgical procedure. As will be described in greater detail below, the system 10 may monitor one or more muscles of the subject 14 for a neuromuscular response that is indicative of a stimulus-induced depolarization of a nerve (i.e., an artificially induced neuromuscular response). If a response of the muscle to the stimulus is detected during the procedure, the system 10 may provide an alert or indication to the surgeon, which may enable the surgeon to take an appropriate action if such action is warranted.

As used herein, an "artificially induced neuromuscular response" is a response of a muscle to a depolarizing stimulus that is applied to a nerve innervating the muscle. In general, the response is "artificially induced" because the nerve is depolarized directly by the stimulus, instead of, for example, the stimulus being received through an intermediate sensory means (e.g., sight, sound, taste, smell, and touch). An example of a stimulus that may cause an "artificially-induced" muscle response may include an electrical current applied directly to the nerve or to intracorporeal tissue or fluid immediately surrounding the nerve. In such an example, if the applied electrical current is sufficiently strong and/or sufficiently close to the nerve, it may artificially cause the nerve to depolarize (resulting in a corresponding contraction of the muscle or muscles innervated by that nerve).

During an artificially induced neuromuscular response, a muscle innervated by the artificially depolarized nerve may physically contract or relax (i.e., a mechanical response) and/or the electrical potential throughout the muscle may be altered. Mechanical responses may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state.

The neural monitoring system 10 may generally include a host system 20 and a sensing device 30 that may cooperate to detect a neuromuscular response of a muscle to a stimulus 42 provided by a stimulator 40. As schematically shown in FIG. 1, the host system 20 may include one or more input devices 22 that are operative to receive information from the surgeon, one or more output devices 24 that are operative to communicate alerts or to provide informational feedback to the surgeon, communication circuitry 26 operative to communicate with the sensing device 30, and a processor 28 that is operative to at least manage the flow of information between the input devices 22, output devices 24 and communication circuitry 26.

In general, the one or more input devices 22 may include a keyboard, a mouse, and/or a digitizer provided with a touch-screen display. These devices may receive pre-operative case information or may permit a surgeon to alter various intraoperative parameters, alarm limits, or other case information before or during a procedure. In some embodiments, the stimulator 40 and/or a foot pedal 44 may provide additional input to the host system 20. This input may be in the form of an analog or digital signal that is indicative of the delivery and/or magnitude of a stimulus. The output device 24 may include, for example, a visual display such as an LED/LCD display 100 (further illustrated in FIG. 3), one or more indicator lights, or speakers capable of providing an audible alert to the surgeon.

The sensing device 30 is the portion of the system 10 that directly contacts the subject 14 and is responsible for, at a minimum, sensing/detecting neuromuscular responses of the subject 14. The sensing device 30 may include a carrier material 32 that is operative to be secured to the subject 14, and a plurality of neuromuscular sensors 34 that are coupled with the carrier material 32 and each operative to monitor a neuromuscular response of a different muscle group of the subject 14. The sensing device 30 may further include communication circuitry 36 that is operative to digitally communicate with the communication circuitry 26 of the host system 20, and a local processor 38 that is in communication with the plurality of neuromuscular sensors 34 and with the communication circuitry 36. In general, processors used with the present system 10 (e.g., processors 28, 38) may each be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

While the specific nature of the sensing device 30 and carrier material 32 may vary based on the location of the surgical site and nature of the surgical procedure, in some embodiments, the carrier material 32 may resemble a cuff or sleeve that is secured around a limb of the subject. Such a design may be suitable, for example, with a spinal procedure where nerves existing within the surgical site are known to innervate peripheral muscles of the arms or legs.

In some embodiments, the carrier material 32 may be a separate therapeutic or diagnostic device that is already common in surgical applications. For example, in a spinal procedure involving one or more of the L2-S1 vertebrae, it is known that nerve roots innervating the leg muscles may lie within the surgical area. During such procedures, however, compression-type anti-embolism stockings (Thrombo-Embolic-Deterrent ("TED") hose) are typically provided around a subject's legs and feet to discourage blood clot formation. Thus, in one embodiment the carrier material 32 may be an elastic sleeve/stocking configured to apply a compressive force to the subject's leg when worn, thus eliminating the need for separate TED hose. Such a compression against the subject may present itself as an elastic tension/strain in the carrier material itself (also referred to as a "tension fit"). In surgical procedures performed higher on the spine, the carrier material 32 may include, for example, a blood pressure cuff worn around the subject's arm (or else may include functionality similar to that of a standard blood pressure cuff). In these examples, the carrier material 32 serves a function outside of that of a dedicated neuromuscular sensing device, and thus provides efficiencies in pre-op preparation and planning, while also allowing monitoring access on sometimes crowded limbs.

In still other embodiments, the carrier material 32 may be a self-adhesive patch that is separate for each sensor. From the perspective of the sensing device 30, the carrier material's main purpose is to hold the neuromuscular sensors 34 in relatively stable contact with the skin of the subject.

While in one embodiment, the neuromuscular sensors 34 can be or can include EMG electrodes, in a more preferred embodiment, the neuromuscular sensors 34 each include a respective mechanical sensor that is operative to monitor a mechanical response of a directly adjacent muscle group. In various embodiments, the mechanical sensor in each neuromuscular sensor 34 may include, for example, a strain gauge, a pressure/force transducer, a position encoder, an accelerometer, a piezoelectric material, or any other transducer or combination of transducers that may convert a physical motion into a variable electrical signal.

As noted above, the system 10 may further include one or more elongate medical instruments 40 (i.e., stimulators 40) that are capable of selectively providing a stimulus 42 within the intracorporeal treatment area 12 of the subject 14. For example, in one configuration, the elongate medical instrument 40 may include a probe 46 (e.g., a ball-tip probe, k-wire, or needle) that has an electrode 48 disposed on a distal end portion. The electrode 48 may be selectively electrified, at either the request of a user/physician, or at the command of the processor 28, to provide an electrical stimulus 42 to intracorporeal tissue of the subject. In other configurations, the elongate medical instrument 40 may include a dilator, retractor, clip, cautery probe, pedicle screw, or any other medical instrument that may be used in an invasive medical procedure. Regardless of the instrument, if the intended artificial stimulus is an electrical current, the instrument 40 may include a selectively electrifiable electrode 48 disposed at a portion of the instrument that is intended to contact tissue within the intracorporeal treatment area 12 during the procedure.

During a surgical procedure, the user/surgeon may selectively administer the stimulus to intracorporeal tissue within the treatment area 12 to identify the presence of one or more nerve bundles or fibers. For an electrical stimulus 42, the user/surgeon may administer the stimulus, for example, upon depressing a button or foot pedal 44 that is in communication with the host system 20. The electrical stimulus 42 may, for example, be a periodic stimulus that includes a plurality of sequential discrete pulses (e.g., a step pulse) provided at a frequency of less than about 10 Hz, or from about 1 Hz to about 5 Hz, and preferably between about 2 Hz and about 4 Hz. Each pulse may have a pulse width within the range of about 50 μs to about 400 μs. In other examples, the discrete pulse may have a pulse width within the range of about 50 μs to about 200 μs, or within the range of about 75 μs to about 125 μs. Additionally, in some embodiments, the current amplitude of each pulse may be independently controllable.

If a nerve extends within a predetermined distance of the electrode 48, the electrical stimulus 42 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, the impedance between the electrical stimulus and the ground patch, and the magnitude of the stimulus current. In one configuration, a lookup table may be employed by the processor 28 to provide an approximate distance between the electrode and the nerve, given a known stimulus magnitude and a measured mechanical muscle response.

As noted above, each mechanical sensor may be specially configured to monitor a local mechanical movement of an adjacent muscle group of the subject 14. In response to this sensed movement, each respective mechanical sensor may generate a mechanomyography (MMG) output signal that corresponds to the sensed mechanical movement, force, and/or response of the adjacent muscle. The MMG output signal may be either a digital or analog signal, and the sensor 34 may further include any communication circuitry or local processing circuitry that may be required to transmit the MMG output signal (or a suitable representation thereof) to the processor 38 via a wired or wireless communications.

The communications circuitry of the sensing device 30 may digitally communicate with the communications circuitry 26 of the host system 20 through any suitable wired or wireless communications means. The respective circuitry 26, 36 may permit unidirectional or bidirectional communications, and may be chosen, in part, according to the number of sensing devices 30 are concurrently used during a procedure (noting that many Bluetooth protocols require point-to-point pairing). Suitable wired protocols include I2C, CAN, TCP/IP, while suitable wireless protocols include IEEE 802.11, Bluetooth, ZigBee, NFC, RFiD or the like.

The following description of setup and operation of the sensing device 30 will be made with respect to a lumbar spinal procedure where the sensing device 30 is provided on a leg of the subject 14. It should be appreciated that the specific nature procedure is illustrative, and should not be read as limiting. The following principles of operation can similarly apply to other procedures, such as spinal procedures performed on the cervical spine (e.g., C5-T1—with the sensing device provided on an arm of the subject), or with other such procedures.

Figure 2:
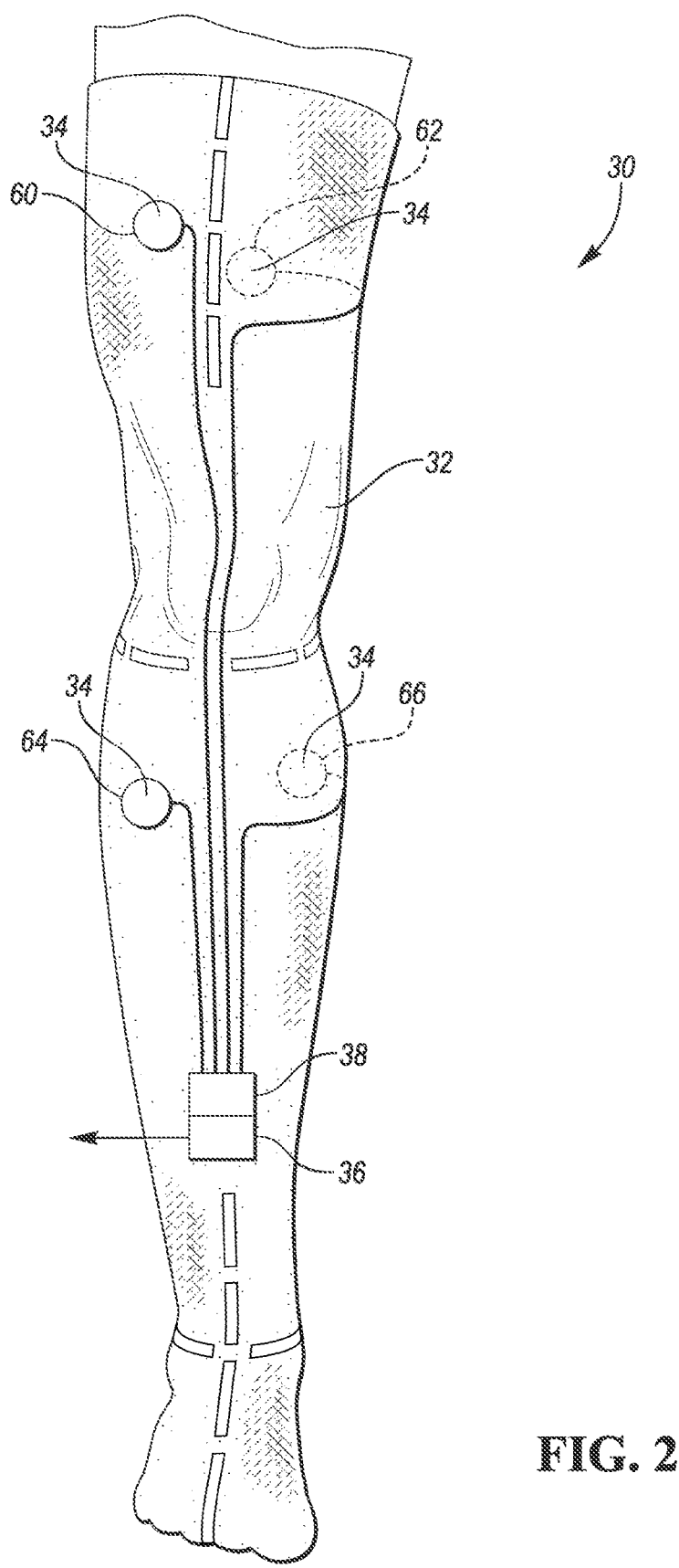
FIG. 2 is an enlarged schematic anterior view of a sleeve-based sensing device provided on a leg of a subject.

FIG. 2 schematically illustrates one embodiment of a sensing device 30 that may be used during the performance of a surgical procedure on the lumbar spine. As shown, in this embodiment, the carrier material 32 may be a sleeve that is operative to maintain an elastic tension fit about a leg of the subject. The sensing device 30 includes a plurality of neuromuscular sensors 34 embedded within, or otherwise directly coupled to the carrier material 32. Each sensor 34 is positioned on the carrier material 32 such that it may monitor a response of a different muscle group of the leg. For example, a first sensor 60 may be located on an anterior portion of the thigh, such that it approximately centered above/outward of the vastus lateralis or vastus medialis muscle when the sleeve is properly positioned on the leg of the subject. A second sensor 62 may be located on a posterior portion of the thigh, such that it approximately centered above/outward of the biceps femoris muscle when the sleeve is properly positioned on the leg of the subject. A third sensor 64 may be located on an anterolateral portion of the lower leg, such that it is approximately centered above/outward of the tibialis anterior muscle when the sleeve is properly positioned on the leg of the subject. Finally, with some procedures lower on the spine, a fourth sensor 66 may be located on the posterior portion of the lower leg, such that it is approximately centered above/outward of the gastrocnemius muscle when the sleeve is properly positioned on the leg of the subject.

Figure 3:
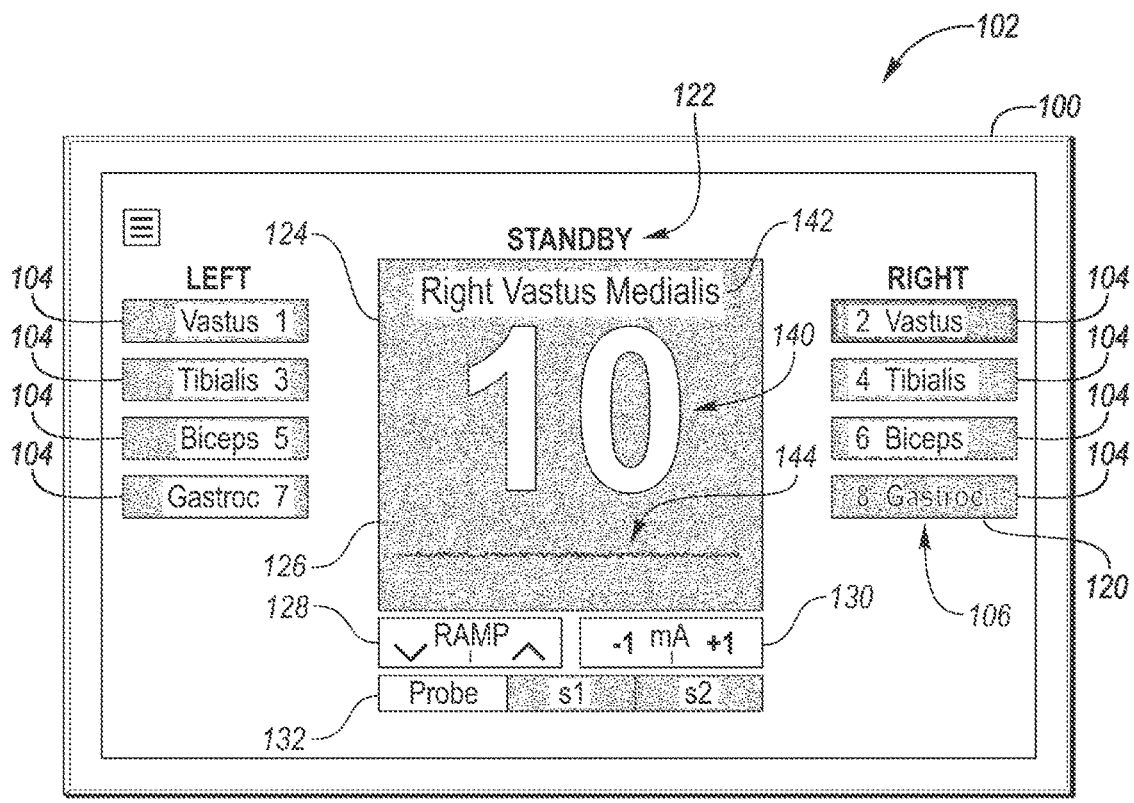
FIG. 3 is a schematic illustration of a display presenting a graphical user interface (GUI) that identifies an intraoperative neural monitoring system as being in a standby state.

During a surgical procedure, the surgeon/user may be presented with a visual indication of the mechanical response detected by each neuromuscular sensor 34 via an LED/LCD display 100 that is associated with the host system 20. FIG. 3 provides one illustration of an informational graphical user interface (GUI) 102 that may be used to present such information. As discussed below, the GUI 102 may have unique characteristics that enable the surgeon to quickly recognize the state of the system, determine if a nerve is proximate to the stimulator, and see the output signal from one or more sensors. Additionally, if multiple sensors are alerting, the user may quickly assess which sensor channel represents a primary response, and which sensor channels are alerting in an ancillary manner.

As shown in FIG. 3, the GUI 102 may include a plurality of icons/display elements 104, with each respective display element 104 representing a different potential sensor channel that could be used within a surgical procedure. The number of display elements 104 should preferably be greater than or equal to the number of sensors 34 in mechanical communication with the subject 14 and/or greater than or equal to the number of muscle groups actively monitored by the sensing device 30.

In some embodiments, the number of display elements 104 may correspond to the number of sensors 34 that are supported by the system. For example, if the system is capable of eight sensing channels, then the GUI 102 may display eight icons 104, each corresponding to a different available sensing channel.

Figure 4:
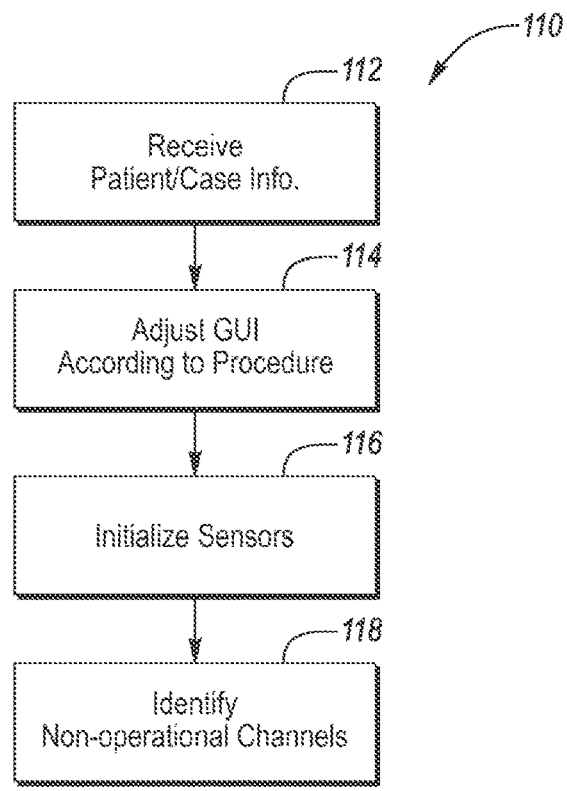
FIG. 4 is a schematic block diagram of a pre-operative setup method for an intraoperative neural monitoring system.

In another embodiment, the number, name, and/or arrangement of each of the plurality of icons 104 may be actively modified according to the nature of the surgery and/or from an actual initialization routine. FIG. 4 schematically represents one embodiment of a pre-op configuration method 110 for preparing the GUI 102 for a surgical procedure. As shown, the method 110 begins at 112 with the user entering patient and/or case-specific information. Using this information, the host system 20 may structure the GUI 102 to include (at 114) a number and arrangement of display elements 104 that corresponds to the nature of the procedure. For example, as shown in FIG. 3, the nature of the procedure may have been entered as a lumbar interbody fusion (LIF) of the L3-L4 spinal vertebrae. From this, the host system 20 may recognize that the implicated nerve roots, and the nerve roots exiting adjacent foramen innervate the primary muscles of the leg (vastus, tibialis, biceps, and gastroc). Therefore, as shown in FIG. 3, the GUI 102 may include display elements 104 corresponding to these respective muscle groups.

In one configuration, the GUI 102 may include the pre-determined, procedure-specific display elements 104 regardless of whether a corresponding sensor is connected. In such an embodiment, the existence of the various display elements may serve as a reminder to affix and initialize the various sensors. In another configuration, the GUI 102 may only include a display element 104 if the corresponding sensor is attached. For example, in the example shown in FIG. 3, if the surgeon was confident that the procedure was limited to the left side, he may choose to omit sensor placement on the right side. In such an embodiment, the display elements corresponding to the muscles of the subject's right leg (i.e., elements 106, collectively) may be hidden from view either by the surgeon or automatically by the system.

With continued reference to FIG. 3, in addition to the display elements 104 corresponding to the various sensors/sensor channels, the GUI 102 may include a central status window 126, a ramp input element 128 for initiating a gradual increase or decrease in the stimulus current over time, a current control element 130 for causing a discrete change in the stimulus current (e.g., in a 0.5 mA or 1 mA increment), and a probe selector element 132 for changing which stimulator 40 (in FIG. 1) is being controlled by elements 128, 130 if more than one stimulator is being used.

The central status window 126 may then include an indication 140 of the stimulus intensity, while also providing the user with the ability to selectively monitor one of the sensor channels. In doing so, the central status window 126 may include a textual indicator 142 that expresses which channel is being monitored (i.e., the "displayed channel"), along with a graph element 144 (better shown in FIG. 6) that graphically represents the real-time MMG output signal from the selected sensor. During use, the displayed channel may be manually selected by tapping on a respective sensor display element 104. For example, as shown in FIG. 3, the user has selected the Right Vastus channel, which is reflected, both by a change in the appearance of the respective display element 104, as well as textually at 142.

Once the sensors 34 are positioned on the subject 14, the host system 20 may then perform an initialization routine (at 116 in FIG. 4) to ensure that each sensor is operational and coordinated to the correct display element 104. In an embodiment, the initialization routine 116 may instruct the user, via the GUI 102, to tap on each sensor in a sequential manner. For example, it may prompt the user to first tap on the left vastus sensor. It may then listen for one sensor channel to transmit an MMG output signal corresponding to an external tap. If multiple sensor channels report a tap-like signal, the host system 20 may report an error or else re-prompt the user via the GUI 102. Once one single channel is identified in response to the prompt, the system 20 may then prompt the user to tap on a different sensor (e.g., left tibialis). This process may continue until each display element 104 is associated with a single sensor response. This manner of sensor initialization and coordination both ensures that there is an operational and responding sensor on each respective muscle group, while also relying on the user's expertise and anatomical knowledge to ensure proper sensor association to the various display elements 104.

While the tap-based manner of sensor initialization is a valuable technique for ensuring that each sensor is operational, other techniques are available for coordinating the various sensors 34 with the display elements 104. In such embodiments, however, the user feedback can also be used to provide a confirmation that the system's understanding of sensor placement and coordination with the display elements 104 is correct. It should be recognized, however that physical user confirmation, such as by tapping, is not strictly required. In some embodiments, sensors may be deemed operational solely by the presence of a transmitted MMG output signal.

In one embodiment, the sensors 34 may each have a unique network address or identifier that is used to preface communications with the host system. In a system where the sensors are provided in a predefined array, such as on an elastic sleeve or cuff, the address may convey the relative location of the sensor within the array. In some embodiments where the array is keyed to the user's body (e.g., including a feature that aids in alignment such as a glove, sock, or indicia that is intended to be anatomically aligned), the address may convey an absolute position of the sensor or a primary muscle group that is being sensed.

In still another embodiment, the host system 20 may make a preliminary estimation of sensor-muscle correspondence by analyzing how the sensor is oriented on the body (e.g., via an accelerometer that can sense a gravity vector). Such a technique is described in Ser. No. 16/158,734, filed on 12 Oct. 2018 (the '734 Application), which is incorporated by reference in its entirety. As described in the '734 Application, general orientation of the sensing device 30 may be determined in a global coordinate frame by examining a static component of one or more MMG output signals, i.e., where the static component is representative of the force of gravity. Given a patient's known posture, the gravity heading will inform the system about which side of the limb the sensor is positioned on. This understanding, together with the knowledge of where various sensors are located across the array/device 30 may allow the system to infer muscle correspondence. In addition to estimating the muscle correspondence, the system may also determine which side of the body the sensing device is positioned on by examining the gravity vector heading on sensors placed on asymmetric portions of the body, such as further discussed in the '734 Application. In one configuration, this concept of gravity-informed sensor coordination may be enhanced by prompts to the user, for example, to lift a particular limb, where distal sensors would have greater travel and rates of acceleration than proximal sensors.

Referring again to FIG. 4, once the operational status and correspondence of the sensors 34 with the display elements 104 is established (at 116), the GUI 102 may then reflect any sensors that are not operational (at 118), such as by highlighting the corresponding display element (e.g., display element 120 in FIG. 3) with an indicia (e.g., a red "X") or by coloring it a different color (represented by the stippling pattern). Following this, the GUI 102 may convey the system's operational status (at 118) for example, to reflect that the system is set up and ready to stimulate, though presently in a standby state. As shown in FIG. 3, the system status (e.g., in standby) may be reflected by a textual status indicator 122 and/or by a visual indicator 124 such as the color of a portion of a portion of the screen.

Figure 5:
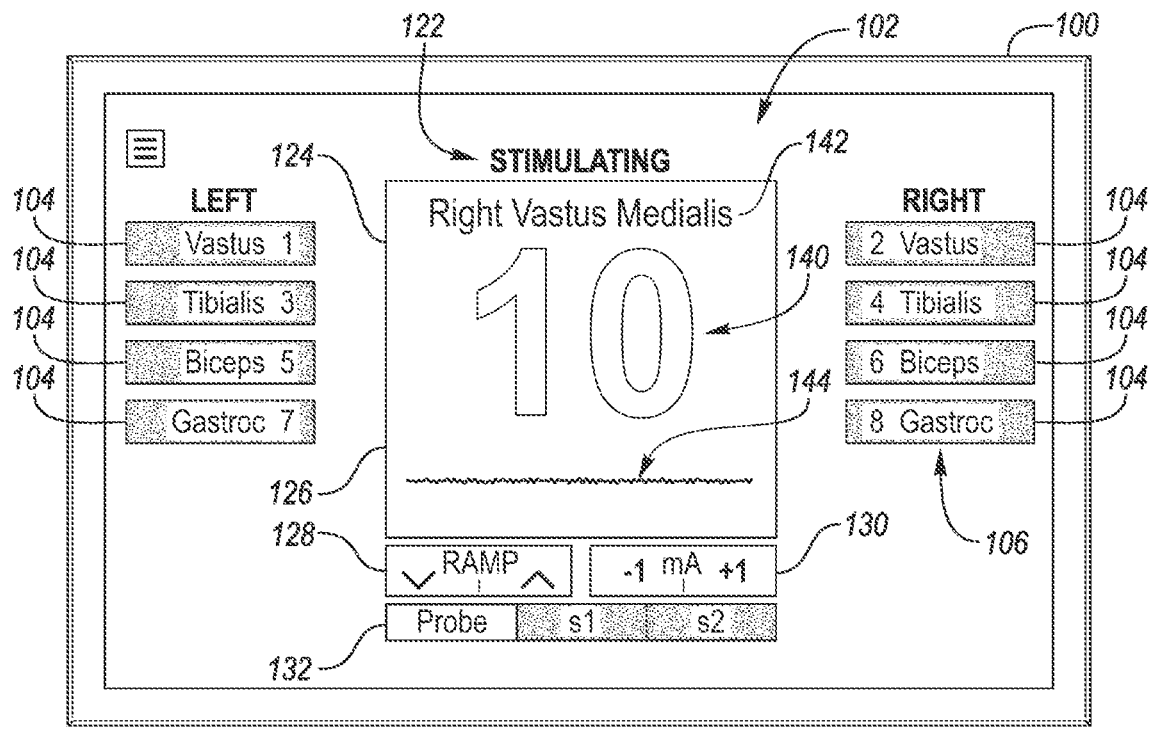
FIG. 5 is a schematic illustration of a display presenting a GUI that identifies an intraoperative neural monitoring system as stimulating without any detected muscle response.

Referring to FIG. 5, once the stimulus beings to be administered, the GUI 102 may be altered to reflect that the system is now in a detection mode. For example, the textual status indicator 122 may reflect "stimulating" and/or a visual indicator 124, such as the color of the background of the central status window 126, may be altered to reflect the stimulating state. In one embodiment, a "standby" state may be reflected, for example, by a first color (e.g., gray), while the "stimulating" state may be reflected, for example, by a second color (e.g., green).

In one embodiment, the system may determine that the stimulator 40 is actively stimulating, for example, by referencing the commanded state (i.e., commanding a power transistor to conduct), however, it may be more informative to sense (e.g. via a sense resistor, current shunt, or inductive current sensor) that the stimulus is actually being administered to the subject. Such sensing may occur at or proximate to one or both of the probe or a ground-return patch that is attached to the subject's body. In this manner, the system may know not just that electrical current is being commanded, but that it is actually being transmitted to/through the subject's body. A loss of good contact between the stimulator and the subject may compromise the validity of the results, however, this may be detected by active monitoring.

Following the administering of the stimulus, the system may monitor the output from the various sensors to determine if there is an evoked muscle response sensed by any of the active sensors. The determination of an evoked muscle response may occur in the time domain, such as described, for example, in U.S. Pat. Nos. 8,343,079 and 8,343,065, which are incorporated by reference in their entirety, in the frequency domain, such as described in U.S. Patent Publication Nos. 2015/0051506 and 2015/0051507, which are incorporated by reference in their entirety, or through the use of pattern recognition techniques, neural networks, or other machine learning algorithms such as described, for example, in U.S. patent application Ser. No. 15/995,879. Analog detection techniques may, for example, compare the time derivative of acceleration of a muscle response to a threshold (i.e., where artificially induced responses have greater da/dt values than natural or externally influenced responses). Frequency-based detection techniques may examine the frequency spectrum of the muscle response to determine if the response has any fundamental frequency or harmonic correspondence to the stimulation frequency. Finally, pattern recognition techniques may analyze an individual sensor output, or the output from a grouping of sensors to recognize patterns that are indicative of an evoked/induced response.

Figure 6:
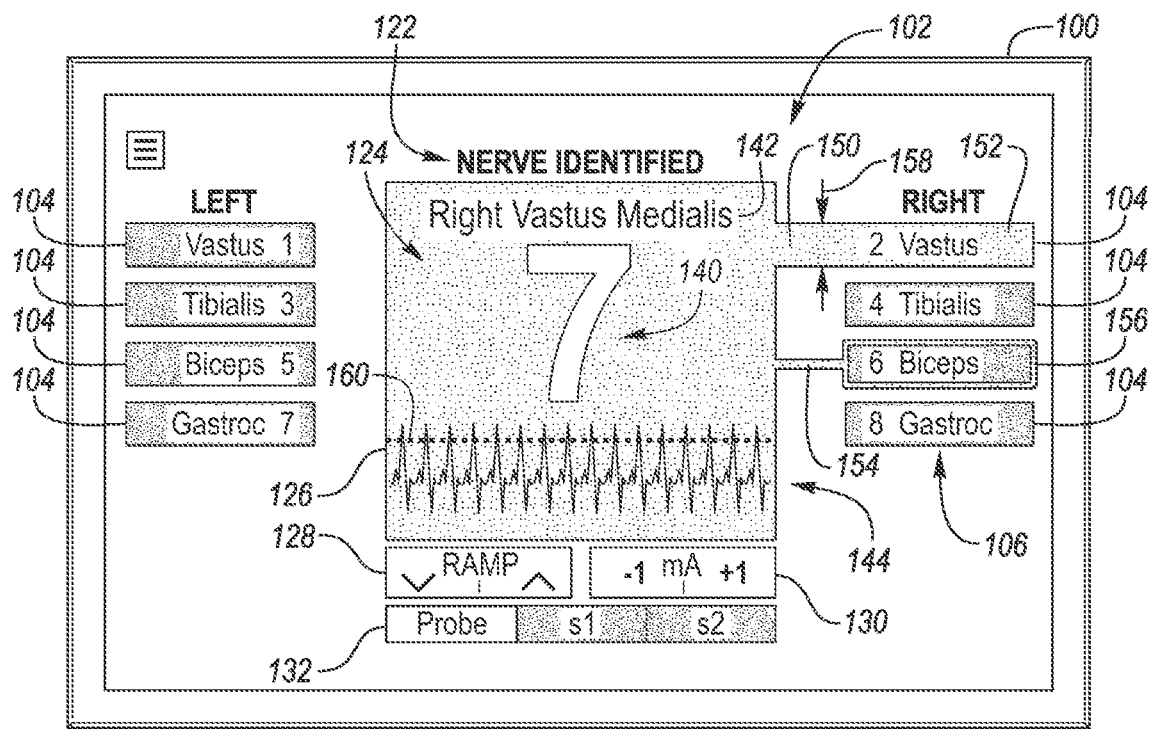
FIG. 6 is a schematic illustration of a display presenting a GUI that identifies an intraoperative neural monitoring system as stimulating and detecting an artificially induced muscle response.

If an evoked muscle response is detected, the GUI 102 may be altered, such as shown in FIG. 6, to reflect that the system has detected an evoked muscle response (i.e., one that is caused directly by the applied stimulus—also referred to as an artificially induced muscle response). For example, the textual status indicator 122 may reflect "Nerve Identified" and/or a visual indicator 124, such as the color of the background of the central status window 126, may be altered to reflect the detected evoked response. In one embodiment, where the "standby" state may be reflected by a first color (e.g., gray), and the "stimulating" state may be reflected by a second color (e.g., green), the "evoked response" state may be reflected, for example, by a third color (e.g., yellow).

As further illustrated in FIG. 6, the GUI 102 may also change the displayed channel to the channel that best evidences the induced muscle response. Because a single nerve root often innervates multiple muscles to varying degrees, if multiple muscle groups were to concurrently evidence an evoked response (i.e., by one or more of the techniques described above), the GUI 102 would, at a minimum, be altered to display the "primary muscle response." In one configuration, the primary muscle response is the sensed response that has the maximum amplitude or magnitude. In another configuration, the primary muscle response would be the evoked muscle response that is the greatest when scaled relative to that muscle's supermaximal response (i.e., the measured response divided by supermaximal response), also referred to as the greatest scaled response.

In one configuration, the GUI 102 may further draw a visual connection between the sensor display element 104 representing the primary muscle response and the central status window 126. For example, in one configuration, the GUI 102 may represent a thick bar 150 between the primary sensor display element 152 and the central status window 126. This may provide a quick visual indication of which channel is being displayed and/or is primarily responding. Additionally, so that lesser responding channels are not simply ignored, a thinner bar 154 may join such ancillary channel sensor elements 156 (i.e., lesser relative response than the primary response) and the central status window 126. In one configuration, the thickness 158 of each bar may correspond to the relative magnitude of the response on that respective channel. It should be understood that the presently described visual techniques are illustrative of a manner of displaying the relative response intensities of different muscles that are artificially induced to respond. Other visual techniques may similarly be used without departing from the spirit of the present disclosure.

As further illustrated in FIG. 6, in some embodiments, a threshold 160 may be overlayed on the graph element 144. The threshold 160 may generally correspond to a physical distance (i.e., a "clearance distance") that the user would like to maintain between the stimulator probe 40 and any nerve while performing the procedure. If the magnitude of the sensed response exceeds the threshold, the textual status indicator 122 may reflect "Alert" and/or a visual indicator 124, such as the color of the background of the central status window 126, may be altered to reflect the response exceeding the threshold. For example, the "Evoked Alert" state may be reflected, for example, by a fourth color (e.g., red).

While the user is making an approach toward a subject's spine, it is important to understand both when there is and when there isn't an evoked response. More specifically, the lack of a response (e.g., a green screen) will affirmatively convey a measure of safety to the user. Certain procedures, however, may involve techniques that are not always suitable for stimulation (thus limiting ability to sense an evoked response). These techniques may involve general gross manipulation of the subject, local manipulation of tissue, or other similar techniques such as muscle retraction. Such techniques, however, still pose some risks that a nerve will be stretched or strained in some way. To alert the user of the possibility of such an event, the system may be configured to monitor each sensor 34 for the occurrence of spontaneous MMG events. These are muscle events that are not caused by an affirmatively administered stimulus (e.g., an electrical stimulus), but rather by actions such as tissue manipulation or prolonged nerve compression.

Spontaneous MMG events may generally be detected by examining the MMG output signal such as described in US 2015/0051507, or in U.S. patent application Ser. No. 15/995,879.

Figure 7:
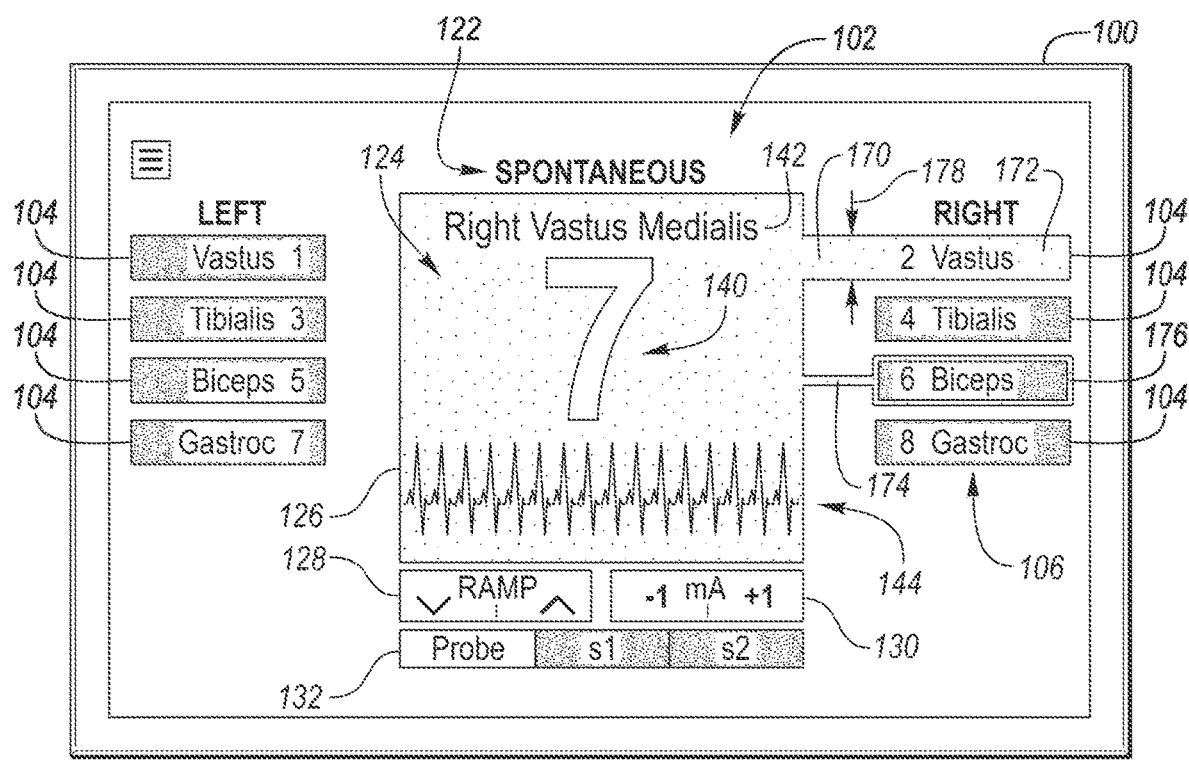
FIG. 7 is a schematic illustration of a display presenting a GUI that identifies an intraoperative neural monitoring system as stimulating and detecting a spontaneous muscle response.

Similar to the evoked response, if a spontaneous muscle response is detected, the GUI 102 may be altered, such as shown in FIG. 7, to reflect that the system has detected a spontaneous muscle response. For example, the textual status indicator 122 may reflect "Spontaneous" and/or a visual indicator 124, such as the color of the background of the central status window 126, may be altered to reflect the detected spontaneous response. In one embodiment, the "spontaneous" state may be reflected, for example, by a fifth color (e.g., blue).

As further illustrated in FIG. 7, similar to the evoked response screen in FIG. 6, the GUI 102 may also change the displayed channel to the channel that detected the primary muscle response. Much like the evoked response, depending on the nerve that is manipulated, the response may be detected across multiple channels/sensors, with one likely being stronger than the other. As such, to highlight the primary response, the GUI 102 may draw a visual connection between the sensor display element 104 representing the primary spontaneous muscle response and the central status window 126. For example, in one configuration, the GUI 102 may represent a thick bar 170 between the primary sensor display element 172 and the central status window 126. Additionally, so that lesser responding channels are not simply ignored, a thinner bar 174 may join such ancillary channel sensor elements 176 (i.e., lesser relative response than the primary response) and the central status window 126. In one configuration, the thickness 178 of each bar may correspond to the relative magnitude of the response on that respective channel.

With reference to FIGS. 3 and 5-7, it should be appreciated that differing stipple patterns represent different colors. While the specific colors are not critical to the implementation of the present technology, it is important that a sufficient amount of contrast be maintained between the colors or imagery so that a user may be immediately alerted with a quickly recognizable and informative prompt. Ultimately, response time when dealing with relatively inelastic nerves or when detecting clearance distances on a millimeter scale is of the utmost importance. As such, the present disclosure provides a system that is capable of maximizing the quantity of information along with the readability of alerts.

While the best modes for carrying out the present technology have been described in detail, those familiar with the art to which this technology relates will recognize various alternative designs and embodiments that are within the scope of the appended claims. It is intended that all matter contained in the above description or shown in the accompanying drawings shall be interpreted as illustrative only and not as limiting.

The invention claimed is:

1. A neuromuscular sensing method comprising:
transmitting an electrical stimulus from a distal end portion of an elongate stimulator extending within an intracorporeal treatment area of a subject;
detecting an artificially induced response of at least two muscles of the subject in response to the transmitted electrical stimulus, each response detected by a respective sensor in mechanical communication with the muscle;
transitioning a graphical user interface (GUI) displayed on a display from a first state to a second state;
the first state indicating to the transmission of a stimulus with no artificially induced response detected; and
the second state indicating the detection of the artificially induced response of the at least two muscles, and further identifying one of the at least two muscles as a primary muscle response.

2. The neuromuscular sensing method of claim 1, wherein the second state further identifies at least one of the at least two muscles as an ancillary muscle response.

3. The neuromuscular sensing method of claim 2, wherein the GUI displays a graph of a sensed amplitude of the response of the muscle corresponding to the primary muscle response.

4. The neuromuscular sensing method of claim 2, further comprising displaying, via the GUI, a relative difference in magnitude between an amplitude of the primary muscle response and an amplitude of the ancillary muscle response.

5. The neuromuscular sensing method of claim 4, wherein displaying the relative difference in magnitude comprises displaying a first element having a first size corresponding to the amplitude of the primary muscle response and displaying a second element having a second size corresponding to the amplitude of the ancillary muscle response.

6. The neuromuscular sensing method of claim 5, wherein the first element comprises a first bar connecting an identification of the muscle corresponding to the primary muscle response with a central display area;

wherein the second element comprises a second bar connecting an identification of the muscle corresponding to the ancillary muscle response with the central display area; and wherein the first size is a thickness of the first bar, and the second size is a thickness of the second bar.

7. The neuromuscular sensing method of claim 1, further comprising transitioning the GUI from the first state to a third state, the third state indicating a detection of a spontaneous response of the at least two muscles, and further identifying one of the at least two muscles as a primary muscle response.

8. The neuromuscular sensing method of claim 1, further comprising displaying, via the GUI, a plurality of display elements, each display element corresponding to a different one of the at least two muscles of the subject;

receiving an input from a user to select one of the plurality of display elements;

displaying a graph of a sensed amplitude of a response of the muscle corresponding to the selected display element.

9. The neuromuscular sensing method of claim 8, further comprising determining correspondence between each of the plurality of display elements and each of the at least two muscles of the subject.

10. The neuromuscular sensing method of claim 8, further comprising providing an indication, via the corresponding display element, if any a sensor in mechanical communication with a muscle is inoperative.

11. The neuromuscular sensing method of claim 8, wherein each of the respective sensors is a mechanical sensor; and wherein detecting an artificially induced response of the at least two muscles of the subject comprises monitoring the mechanical motion of each of the at least two muscles using the respective mechanical sensor in mechanical communication with the muscle.

12. An intraoperative neural monitoring system comprising:

a plurality of mechanical sensors, each operative to monitor a different muscle of a subject;

an elongate stimulator operative to extend within an intracorporeal treatment area of a subject and to transmit an electrical stimulus from a distal end portion;

a host system in communication with the plurality of mechanical sensors, the host system including a display and a processor, the processor configured to:

receive an output signal from each of the mechanical sensors, the output signal corresponding to the movement of the monitored muscles of the subject;

display a graphical user interface (GUI) via the display;

detect an artificially induced response of at least two muscles of the subject in response to the electrical stimulus, each response detected from the received output signals; and transition the GUI from a first state to a second state in response to the detected artificially induced response of the at least two muscles;

the first state indicating the transmission of a stimulus with no artificially induced response detected; and the second state indicating the detection of the artificially induced response of the at least two muscles, and further identifying one of the at least two muscles as a primary muscle response.

13. The intraoperative neural monitoring system of claim 12, wherein the second state further identifies at least one of the at least two muscles as an ancillary muscle response.

14. The intraoperative neural monitoring system of claim 13, wherein the processor is further configured to display, via the GUI, a graph of a sensed amplitude of the response of the muscle corresponding to the primary muscle response.

15. The intraoperative neural monitoring system of claim 13, wherein the processor is further configured to display, via the GUI, a relative difference in magnitude between an amplitude of the primary muscle response and an amplitude of the ancillary muscle response.

16. The intraoperative neural monitoring system of claim 15, wherein the processor is further configured to display the relative difference in magnitude by displaying a first element having a first size corresponding to the amplitude of the primary muscle response and displaying a second element having a second size corresponding to the amplitude of the ancillary muscle response.

17. The intraoperative neural monitoring system of claim 16, wherein the first element comprises a first bar connecting an identification of the muscle corresponding to the primary muscle response with a central display area;

wherein the second element comprises a second bar connecting an identification of the muscle corresponding to the ancillary muscle response with the central display area; and wherein the first size is a thickness of the first bar, and the second size is a thickness of the second bar.

18. The intraoperative neural monitoring system of claim 12, wherein the processor is further configured to detect a spontaneous response of at least two muscles of the subject, each response detected from the received output signals; and transition the GUI from the first state to a third state, the third state indicating the detection of a spontaneous response of the at least two muscles, and further identifying one of the at least two muscles as a primary muscle response.

19. The intraoperative neural monitoring system of claim 12, wherein the processor is further configured to:

display, via the GUI, a plurality of display elements, each display element corresponding to a different one of the plurality of mechanical sensors;

receive an input from a user selecting one of the plurality of display elements; and display a graph of the output of the mechanical sensor corresponding to the selected display element.

20. The intraoperative neural monitoring system of claim 12, wherein the processor is further configured to:

detect one or more display elements that do not correspond to an operational mechanical sensor; and provide a visual indication of the one or more display elements that do not correspond to an operational mechanical sensor.

* * * * *